United States Patent [19]
Kittelsen et al.

[11] Patent Number: 5,353,810
[45] Date of Patent: Oct. 11, 1994

[54] WISHBONE TETHER FOR MOUTHGUARD ASSEMBLIES

[75] Inventors: Jon D. Kittelsen, Fridley; Paul C. Belvedere, Edina, both of Minn.

[73] Assignee: E-Z Gard Industries, Inc., Minneapolis, Minn.

[21] Appl. No.: 62,788

[22] Filed: May 14, 1993

[51] Int. Cl.⁵ .............................................. A61C 5/14
[52] U.S. Cl. .................................. 128/862; 128/861; 128/859
[58] Field of Search ...................... 128/861, 862; 433/6

[56] References Cited

U.S. PATENT DOCUMENTS

| | | | |
|---|---|---|---|
| 2,708,931 | 5/1955 | Freedland | 128/861 |
| 3,058,462 | 10/1962 | Greenblum | 128/136 |
| 3,082,765 | 3/1963 | Helmer | 128/136 |
| 3,682,164 | 8/1972 | Miller | 128/136 |
| 4,330,272 | 5/1982 | Bergersen | 433/861 |
| 4,348,178 | 9/1982 | Kurz | 433/861 |
| 5,152,301 | 10/1992 | Kittelsen et al. | 128/861 |

Primary Examiner—Robert A. Hafer
Assistant Examiner—Michael O'Neill
Attorney, Agent, or Firm—Palmatier, Sjoquist & Helget

[57] ABSTRACT

A wishbone tether is provided for remote anchor attachment of the mouthguard assembly which is worn by the user to protect the teeth, tongue, mouth and lips of the user. The wishbone tether has a U-shaped portion extending from the canine regions of the mouthguard to permit clearance at the forward end of the mouthguard for the unhindered movement of the tongue and lips for clear speaking while wearing the mouthguard assembly. A tab remote connecting portion extends forwardly from the U-shaped portion having attachment structure for remote attachment of the wishbone tether and mouthguard assembly to a remote anchor chosen from a group comprising of a helmet, a headgear, a face mask and an user's neck.

4 Claims, 2 Drawing Sheets

WISHBONE TETHER FOR MOUTHGUARD ASSEMBLIES

BACKGROUND OF THE INVENTION

The present invention generally relates to a protective mouthguard assembly for use in athletics and more particularly to a wishbone tether for remote attachment of a mouthguard assembly which permits unhindered movement of the tongue and lips for clear speaking while wearing the mouthguard.

A number of mouthguards currently exist in the art for protecting the teeth, gums, tongue and lips and for further reducing the chance of shock, concussion or other injury as a result of high impact collisions and blows during athletic competition. In general, mouthguards existing in the art can be placed in two broad categories: tethered and untethered.

Untethered mouthguards are commonly fabricated by the user applying the boil-and-bite methodology or by dentists who fit the mouthguard to the exact contour of the user's teeth. These mouthguards are manufactured in a single configuration. The mouthguard may also be trimmed to the correct size with a scissors to assist in comfortably forming the mouthguard to fit to the contour of the user's teeth and mouth.

In certain athletic activities, which utilize a helmet or other protective headgear, and in particular in high impact sports such as football and hockey, it is desirable for the mouthpiece to be tethered to the helmet, headgear, face mask or about the user's neck. The principal reasons are twofold. First, having the mouthguard tethered to the helmet or face mask eliminates the chance that the mouthguard will be lost or misplaced. Secondly and perhaps most important, a number of instances have occurred where the user inadvertently swallows the mouthguard as a result of impact or otherwise during physical activity. This can result in the user choking on the mouthpiece, thus causing severe injury or death.

The tethered mouthpieces that currently exist in the art are generally of a one piece construction comprising a moldable mouthpiece and an integrally formed tether strap constructed of the same material as the mouthpiece and extending from the forward end of the mouthpiece or mouthguard for connection to the helmet or the like. Tethered mouthguards also exist where the tether is removable from the mouthguard.

There is a principal limitation relating to presently existing permanent and removable tethered mouthguards. Because the tether straps are constructed of the same material as the mouthguards, the straps are generally quite wide in order to prevent the straps from inadvertently breaking. As a result, the straps are stiff and cumbersome and often have a relatively limited flexibility. These facts, coupled with the extension of the tether straps from the central region of the forward end of the mouthguard, make it almost impossible and surely difficult for the wearer to clearly speak during athletic activity which is common and necessary in sports such as football, hockey and the like. This speaking difficulty is caused by the obstruction of the tether strap prohibiting the upper and lower lips with the tongue to work together to pronounce and annunciate words clearly.

There is a need for a mouthguard assembly for use in athletic competition that will permit remote and selective anchoring of the mouthguard with a tether strap suitably with a quick release that does not hinder the lips, mouth and tongue to speak, but rather promotes clear annunciation while wearing the tethered mouthguard so needed in many athletic activities.

SUMMARY OF THE INVENTION

A wishbone tether is provided for remote anchor attachment of the mouthguard assembly which is worn by the user to protect the teeth, tongue, mouth and lips of the user. The wishbone tether has a U-shaped portion extending from the canine regions of the mouthguard to permit clearance at the forward end of the mouthguard for the unhindered movement of the tongue and lips for clear speaking while wearing the mouthguard assembly. A tab remote connecting portion extends forwardly from the U-shaped portion having attachment means for remote attachment of the wishbone tether and mouthguard assembly to a remote anchor chosen from a group comprising of a helmet, a headgear, a face mask and an user's neck.

A principal object and advantage of the present invention is the provision of a break-away featured mouthguard assembly having a tether for selective remote anchoring which permits the unhindered movement of the tongue and lips for clear speaking while wearing the mouthguard assembly and participating in athletic activity.

Another object and advantage of the present invention is that the wishbone tether permits the wearer to seal his/her lips, spit or discharge spital from the mouth, wet his/her lips and more easily breath.

Another object and advantage of the present invention is that it contains all the refinements and advantages of past known tether straps adaptable for use with any of a variety of attachment means for remote attachment of the wishbone tether and mouthguard assembly to a remote anchor.

Other objects and advantages will become readily apparent upon reading and study of the following specification, appended claims and attached Figures.

DETAILED SPECIFICATION

Figure 4:
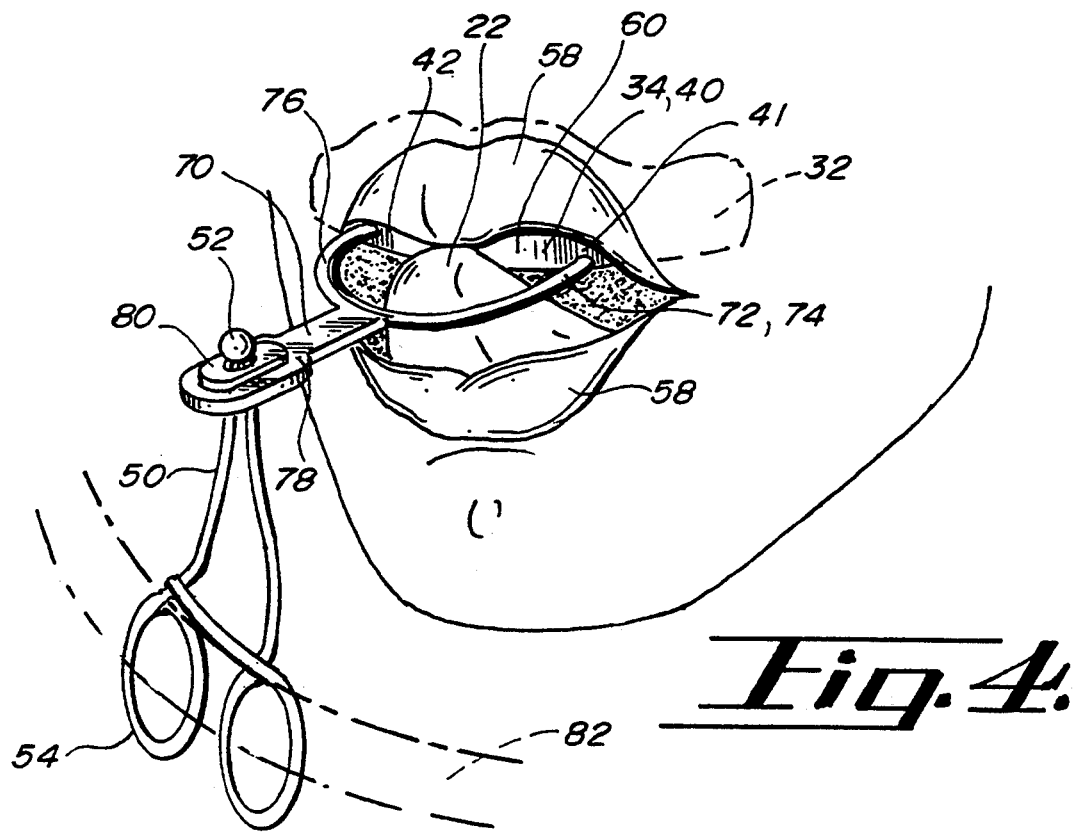
FIG. 4 is a perspective view of a wearer of Applicant's new mouthguard assembly with a wishbone tether.
Figure 5:
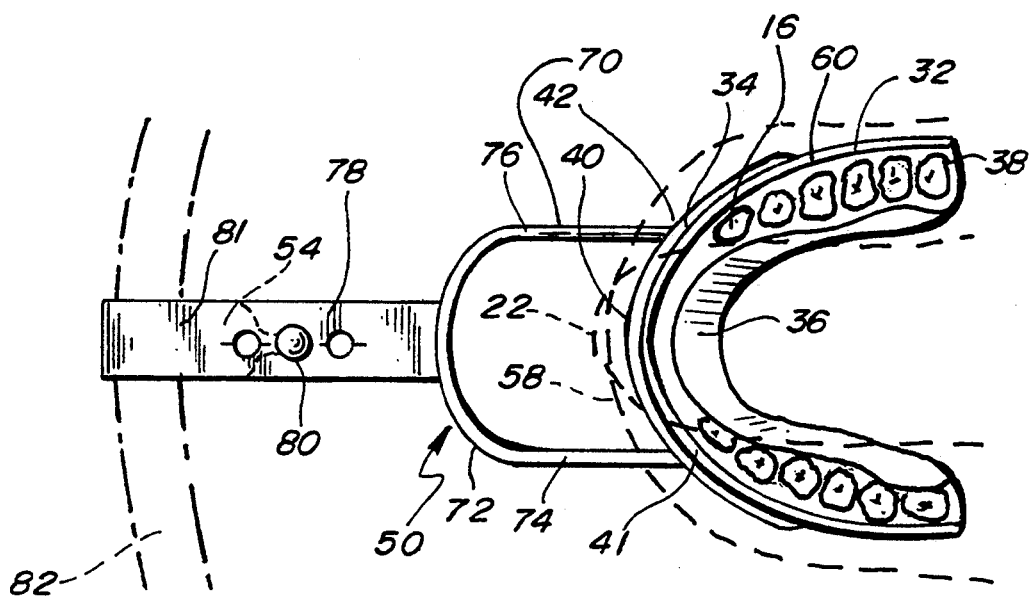
FIG. 5 is a top plan view of the present invention with the wearer's teeth, lips and tongue shown in phantom outline.

The present invention may generally be seen in FIGS. 4 and 5. A mouthguard assembly has connected to its forward end 40 adjacent the canine regions 41 and 42 a wishbone tether 70 which permits the wearer to comfortably speak clearly without interference as from past known tether or tab combinations extending directly from the forward end 40 of a mouthguard assembly.

Figure 1:
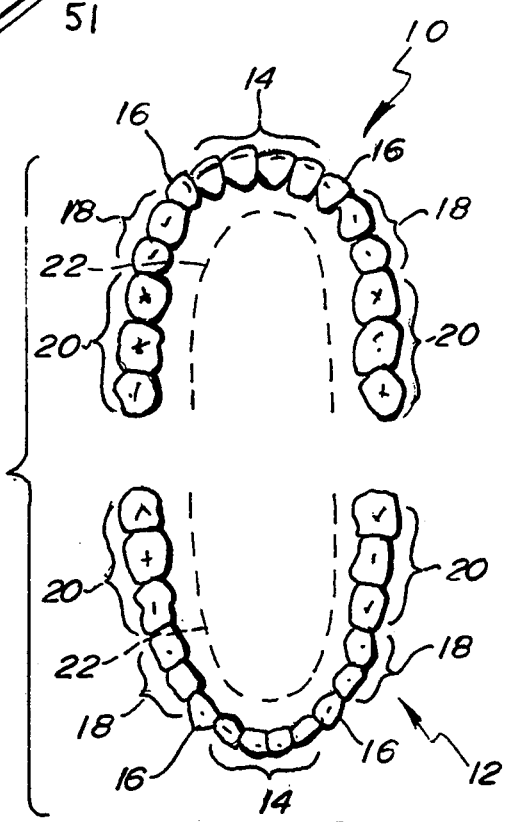
FIG. 1 is a plan view of the upper and lower dentitions of the mouth.

Referring specifically to FIG. 1, the upper and lower dentitions 10 and 12 of a person are shown. The teeth of an individual or person include incisors 14, canine or eye teeth 16, bicuspids 18 and molars 20. The tongue 22 is shown in relation to the dentitions 10 and 12 for illustrative purposes.

Figure 3:
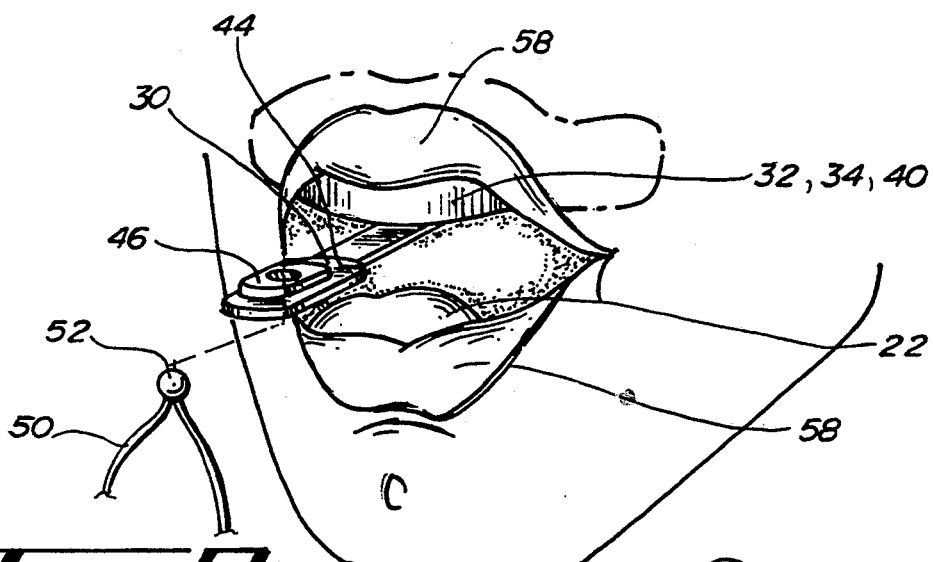
FIG. 3 is a perspective view of a wearer of a prior art mouthguard assembly.
Figure 2:
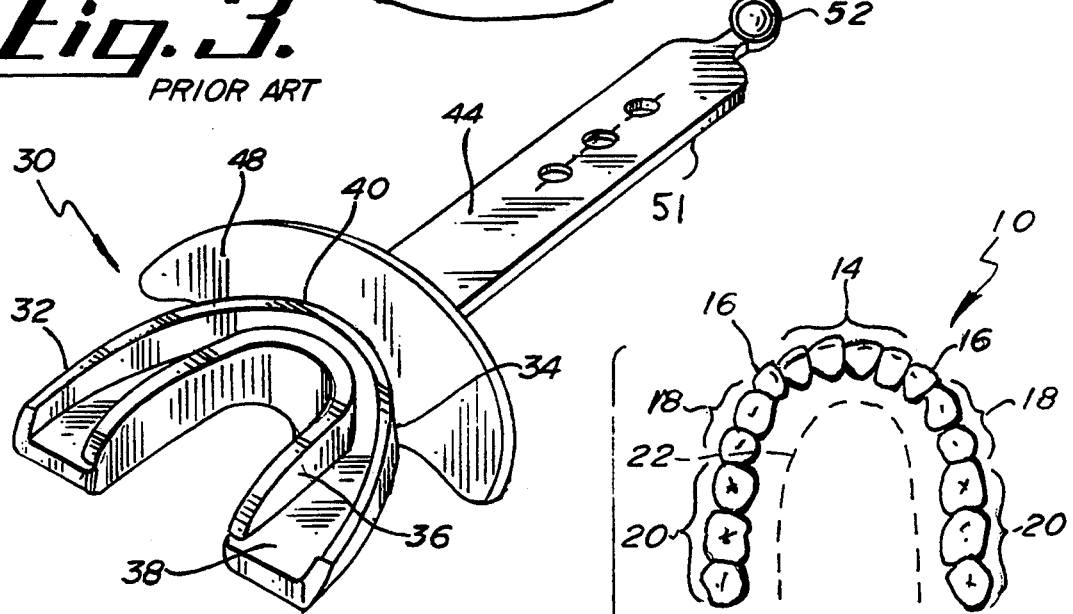
FIG. 2 is a perspective view of a prior art mouthguard assembly.

Referring to FIGS. 2 and 3, a typical prior art mouthguard assembly 30 includes a mouthpiece portion 32 having a forward or outer protective flange 34 and a rearward or inner protective flange 36 connected by a protective web or channel 38. The mouthguard portion 32 may be softened by momentary placement in boiling water afterwhich it is fit and vacuumed against the teeth and gums of the wearer. The mouthguard portion 32 has a forward end 40 with two canine regions 41 and 42. A tab 44 suitably extends and is integral with the forward end 40 of the mouthpiece portion 32.

Referring to FIG. 3, the tab 44 has a tether attachment means 46 in the form of a reinforced aperture for receipt of a tab attachment end or bead 52 of a tether 50 for remote attachment of the tether 50 to an anchor such as a helmet, face mask, headgear or about the user's neck. Referring to FIG. 2, the tab 44 suitably has a shield 48 suitably in position in front of the user's lips 58 as is common in the prior art which further restricts and limits clear speaking by the user. In this prior art embodiment, the tab 44 extends to a tab/tether combination 51 with a tab attachment end or bead 52 which permits securement back upon the tab or tether combination 51, as is known.

Again referring to FIG. 3, the prior art mouthguard assembly 30 is in place and being worn by the user. It is obvious that the tab 44 extending from the forward end 40 prohibits the lips 58 and tongue 22 from interacting correctly together to permit clear speech. The result is the wearer of the mouthguard assembly 30 has garbled speech making it difficult for the wearer to communicate with his fellow athletes during competition.

Referring to FIGS. 4 and 5, the present invention comprising the mouthguard assembly 60 and wishbone 70 may be clearly understood. The invention may be constructed of a variety of thermoplastic type materials while it is contemplated that the preferred embodiment is an ethylene vinyl acetate material.

The mouthguard assembly 60 suitably has a mouthpiece portion 32 with a forward or outer protective flange 34, a rearward or inner protective flange 36 and a protective web or channel 38 therebetween. The mouthpiece portion suitably may be fitted by softening the mouthpiece portion in boiling water and placing the mouthpiece portion 32 over the upper dentition 10. Thereafter the user or wearer applies self-vacuum and presses the outer and inner flanges 34 and 36 to the upper dentition 10 to form the customized mouthpiece portion 32.

The mouthpiece 32 has a forward end 40 and two canine or eye teeth regions 41 and 42. At these canine regions 41 and 42, the wishbone tether 70 forwardly extends. The wishbone tether 70 has a U-shaped portion 72 with a left leg 74 and a right leg 76 integrally formed or welded to the canine regions 41 and 42 of the mouthpiece portion 32.

FIG. 4 reveals how the user or wearer can readily annunciate clearly with freedom of movement and contact of the tongue 22 and lips 58 permitting the athlete to readily, easily and clearly communicate with his fellow athletes during athletic competition.

Extending forwardly from the U-shaped portion 72 is a tab remote connecting portion 78 which has attachment means 80 illustrated in FIG. 4 to be a reinforced aperture for receipt of the attachment bead 54 of a tether 50. This structure facilitates a breakaway feature of the mouthguard assembly 60 from the remote anchor 82. The remote attachment end or loop 54 of the tether 50 may be secured to a facemask 82.

FIG. 5 shows another embodiment of the tab remote connecting portion 78 having a tab extension 81 which wraps about the facemask 82 and secures back onto the attachment means 80. This structure facilitates a breakaway feature of the mouthguard guard assembly 60 from the remote anchor 82. Consequently, the remote connecting tab portion 78 may take various forms while the U-shaped portion 72 of the wishbone tether permits the wearer to easily and clearly speak.

The present invention may be embodied in other specific forms without departing from the spirit of essential attributes thereof; therefore, the illustrated embodiment should be considered in all respects as illustrative and not restrictive, reference being made to the appended claims rather than to the foregoing description to indicate the scope of the invention.

We claim:

1. A wishbone tether and a thermoplastic protective athletic activity mouthguard assembly for protecting the teeth, gums, tongue and lips, the tether for remote attachment of the mouthguard assembly to an anchor, the mouthguard assembly having a mouthguard portion with a forward protective flange, a rearward protective flange and a connecting protective web for receiving and protectively engaging the incisor, canine, bicuspid and molar teeth of the wearer to protect the teeth, tongue and lips of the user, the mouthpiece portion having a forward end and two canine regions, the wishbone tether comprising:

(a) a flexible thermoplastic U-shaped portion having left and right legs each extending from one of the canine regions to permit clearance at the forward end of the mouthguard portion for the unhindered movement of the tongue and lips for clear speaking while wearing the mouthguard assembly; and (b) a flexible thermoplastic tab remote connecting portion extending forwardly and joining the left and right legs of the U-shaped portion and having attachment means releasably attachable to a remote anchor chosen from a group consisting of a helmet, a headgear, or a facemask for remote flexible attachment of the wishbone tether and mouthguard assembly.

2. The wishbone tether of claim 1, wherein the wishbone tether is integral with the mouthguard portion.

3. A wishbone tether and protective mouthguard assembly, the assembly comprising:

(a) a flexible thermoplastic protective athletic activity mouthguard having a mouthguard portion with a forward protective flange, a rearward protective flange and a connecting protective web for receiving and protectively engaging incisor, canine, bicuspid and molar teeth of the wearer to protect the teeth, tongue and lips of the user, the mouthpiece portion having a forward end and two canine regions; and (b) a wishbone tether comprising:

(i) a flexible thermoplastic U-shaped portion having left and right legs each for extending from one of the canine regions to permit clearance at the forward end of the mouthguard portion for the unhindered movement of the tongue and lips for clear speaking while wearing the mouthguard assembly; and (ii) a flexible thermoplastic tab remote connecting portion extending forwardly and joining the left and right legs of the U-shaped portion and having attachment means releasably attachable to a remote anchor chosen from a group consisting of a helmet, a headgear, or a facemask for remote attachment of the wishbone tether and mouthguard assembly.

4. The wishbone tether of claim 3, wherein the wishbone tether is integral with the mouthguard portion.

* * * * *